United States Patent
Hayashi et al.

(12)

(10) Patent No.: US 6,433,345 B1
(45) Date of Patent: Aug. 13, 2002

(54) FLUORESCENCE OBSERVING APPARATUS

(75) Inventors: Katsumi Hayashi; Toshiro Hayakawa; Yoji Okazaki, all of Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 99 days.

(21) Appl. No.: 09/611,972

(22) Filed: Jul. 6, 2000

(30) Foreign Application Priority Data

Jul. 7, 1999 (JP) ............................................. 11-192487
May 16, 2000 (JP) ....................................... 2000-143700

(51) Int. Cl.[7] ................................................. F21V 9/16
(52) U.S. Cl. ................. 250/458.1; 250/459.1; 250/461.1
(58) Field of Search ......................... 250/458.1, 459.1, 250/461.1

(56) References Cited

U.S. PATENT DOCUMENTS

| 4,556,057 A | 12/1985 | Hiruma et al. ............... 600/476 |
|---|---|---|
| 5,323,008 A | 6/1994 | Studholme et al. ......... 250/458.1 |
| 5,523,573 A * | 6/1996 | Hanninen et al. ......... 250/458.1 |
| 5,679,152 A * | 10/1997 | Tischler et al. ................ 117/97 |
| 6,070,096 A * | 5/2000 | Hayashi .................... 250/458.1 |
| 2001/0009269 A1 * | 7/2001 | Hayashi .................... 250/458.1 |
| 2002/0014595 A1 * | 2/2002 | Sendai et al. ............. 250/458.1 |

FOREIGN PATENT DOCUMENTS

| EP | 0 977 028 A1 | 2/2000 | .......... G01N/21/39 |
|---|---|---|---|
| WO | 00/13017 | 3/2000 | .......... G01N/33/53 |

* cited by examiner

Primary Examiner—Georgia Epps
Assistant Examiner—M. Hasan
(74) Attorney, Agent, or Firm—Sughrue Mion, PLLC (57) ABSTRACT

A fluorescence observing apparatus including a light source for emitting excitation light, an excitation light irradiation section for irradiating the excitation light to a sample, and a fluorescence measurement section for measuring fluorescence emitted from the sample by the irradiation of the excitation light. The temperature of the light source is always sensed by a thermistor, and a Peltier element disposed in direct contact with the light source is cooled by a control section so that the temperature of the light source is maintained at 20° C. or less.

22 Claims, 10 Drawing Sheets

FLUORESCENCE OBSERVING APPARATUS

BACKGROUND OF THE INVENTION

1. Field of the Invention

The present invention relates to a fluorescence observing apparatus for measuring fluorescence emitted from a sample (e.g., an organism, etc.) by irradiation of excitation light to provide information which is used for diagnosis, etc.

2. Description of the Related Art

A diagnosis instrument, etc., for acquiring the intensity and spectrum of fluorescence emitted from a sample (e.g., an organism, etc.) by irradiation of excitation light to obtain information which is used for diagnosis, are known. These diagnosis instruments employ a method of detecting fluorescence emitted when excitation light for diagnosis is irradiated to the tissue of an organism, a method of detecting fluorescence emitted by irradiating excitation light to the tissue of an organism which has absorbed a drug for fluorescence diagnosis beforehand, or similar methods. The diagnosis instrument is incorporated into an endoscope, a colposcope, an operation microscope, etc., and is utilized for observation of a fluorescence image.

For example, Japanese Unexamined Patent Publication No. 59(1984)-40830 discloses an apparatus which employs an excimer dye laser as an excitation light source. In this apparatus, the excitation light emitted from this light source is irradiated to the tissue of an organism into which a photosensitive material having tumor affinity has been injected beforehand, and the fluorescence emitted from the tissue is observed. The above-mentioned technique is used for observing the tissue of an organism as a dynamic image by obtaining an image from the tissue at cycles of 1/60 sec and is capable of simultaneously observing a normal image and a fluorescence image as the dynamic image. For observation of the fluorescence image, the excitation light emitted from the excimer dye laser is irradiated to the tissue of an organism (which is a subject) with a pulse width of 30 nsec at cycles of 1/60 sec, and the fluorescence emitted from the tissue by irradiation of the excitation light is imaged by a high-sensitivity imaging device for a fluorescence image. In this way, the dynamic image is obtained. On the other hand, for observation of the normal image, white light is irradiated to the tissue of an organism (which is a subject) at cycles of 1/60 sec, while the aforementioned period of the irradiation of the excimer dye laser which is performed at cycles of 1/60 sec with a pulse width of 30 nsec is being avoided. The obtained images are formed into a dynamic image by an imaging device for a normal image.

Here, the pulsed light emission of an excimer dye laser will be output as pulsed light whose peak value is extremely high, even if the emission time is 30 nsec. Therefore, the intensity of fluorescence being emitted from the tissue subjected to the irradiation is sufficient to obtain satisfactory diagnosis information. In addition, there is almost no time lag between the irradiation of excitation light to the tissue and the emission of fluorescence from the tissue and therefore the irradiation of excitation light and the emission of fluorescence are considered nearly the same. Thus, there is no possibility that the period during which the irradiation of excitation light and the formation of a fluorescence image are performed will overlap with the period during which the irradiation of white light and the formation of a normal image are performed. Furthermore, because the formation of a fluorescence image is performed within the blanking period after the formation of a normal image which is a short time, the rate at which external light and background light (such as indoor illumination) are formed as noise components, along with the fluorescence image is extremely low.

As described above, while excimer dye lasers have many advantages as an excitation light source, the apparatus is extremely large in scale and extremely high in cost. Because of this, employing a small and inexpensive semiconductor laser as an excitation light source has recently been discussed.

The semiconductor laser, however, is weak in light intensity when employed as an excitation light source. In addition, if the semiconductor laser is oscillated to generate a peak value greater than or equal to the continuous maximum rated output value, a phenomenon called catastrophic optical damage (COD) will arise and the end face of the active layer of the semiconductor laser will be destroyed. In this phenomenon, non-radiative recombination occurs from a defect in the end face of the active layer of the semiconductor laser, and non-radiative recombination energy is turned into heat by the thermal vibration of the lattice. Because of this heat, the temperature of the end face rises and dislocation propagates, whereby the bandgap becomes narrower. If the bandgap becomes narrower, the end face further absorbs light and generates heat, resulting in a rise in the temperature of the end face. As a result, thermal runaway takes place and finally melts the end face. Particularly, in the semiconductor laser with a large energy gap, which is employed in an excitation light source to emit light which has a wavelength belonging to a region near ultraviolet rays, it is difficult to emit pulsed light having a peak value greater than or equal to the continuous maximum rated output value. In the case where drive current is increased to forcibly emit high-output light, degradation is conspicuous and there is a danger that a sufficiently long lifetime as a light source for a fluorescence observing apparatus will not be obtained. Also, in the case where laser light, emitted from a semiconductor laser and oscillating continuously, is used to emit high-output light which can be used as an excitation light source for a fluorescence observing apparatus, degradation is conspicuous and there is a danger that a sufficiently long lifetime will not be obtained.

SUMMARY OF THE INVENTION

The present invention has been made in view of the aforementioned problems. Accordingly, it is an object of the present invention to provide a fluorescence observing apparatus equipped with a small and inexpensive light source capable of emitting high-output excitation light. Another object of the invention is to provide a fluorescence observing apparatus which is capable of making the lifetime of the light source sufficiently long.

To achieve the aforementioned objects, there is provided a fluorescence observing apparatus comprising a light source for emitting excitation light, excitation light irradiation means for irradiating the excitation light to a sample, and fluorescence measurement means for measuring fluorescence emitted from the sample by the irradiation of the excitation light, wherein a GaN-based semiconductor laser is employed as the light source and the apparatus further includes temperature-controlling means for controlling the temperature of the semiconductor laser to 20° C. or less.

The aforementioned objects of the present invention are also achieved by a fluorescence observing apparatus comprising a light source for emitting excitation light, excitation light irradiation means for irradiating the excitation light to a sample, and fluorescence measurement means for measuring fluorescence emitted from the sample by the irradiation of the excitation light, wherein a GaN-based semiconductor laser is employed as the light source and the apparatus further includes temperature-controlling means for controlling the temperature of the semiconductor laser to 20° C. or less.

In a preferred form of the present invention, the aforementioned semiconductor laser emits output light greater than or equal to rated output at room temperature.

The aforementioned GaN-based semiconductor laser may be an InGaN-based semiconductor laser. In that case the active layer of the semiconductor laser may have an InGaN/InGaN quantum cell structure.

The aforementioned semiconductor laser may be a broad area type or surface emission type semiconductor laser. It may to also be an array type semiconductor laser.

According to the fluorescence observing apparatus of the present invention, in a fluorescence observing apparatus for irradiating pulsed excitation light emitted from a light source, to a sample (such as an organism, etc.) and measuring fluorescence emitted from the sample, if a GaN semiconductor laser is adopted as the light source and controlled to 20° C. or less, the oscillating threshold current of the GaN semiconductor laser can be reduced and the maximum output is not limited at thermal saturation. As a result, the GaN semiconductor laser becomes able to oscillate with high output. In addition, since the degradation rate of the semiconductor laser becomes lower as temperature becomes lower, the semiconductor can emit high-output excitation light over a long time. Therefore, even if a small and inexpensive GaN semiconductor laser is adopted as an excitation light source for a fluorescence observing apparatus, it can emit high-output excitation light over a long time and have a sufficiently long lifetime.

If the GaN-based semiconductor layer is controlled to 10° C. or less, it can oscillate with even higher output and further prolong its lifetime.

If the aforementioned semiconductor layer emits output light greater than or equal to rated output at room temperature, even higher output can be obtained.

If an InGaN-based semiconductor laser is employed in place of the aforementioned GaN-based semiconductor laser, carriers are inevitably captured at a local level formed due to the composition unevenness of indium (In), etc., before they are captured at a lattice defect from which non-radiative recombination occurs. At the local level, radiative recombination is performed. Therefore, even if a defect such as dislocation is present, non-radiative recombination will not occur from the defect and the injected current can be inhibited from giving rise to generation of heat without being converted to light. As a result, even if a defect such as dislocation is present within the active layer, the occurrence of catastrophic optical damage (COD) can be prevented.

If the active layer of the aforementioned semiconductor laser has an InGaN/InGaN quantum cell structure, a quantum level is formed in the quantum cell and carriers become concentrated in the mini-band. As a result, as the efficiency of radiative recombination becomes better and the oscillating threshold current is reduced, higher light output can be obtained with less drive current.

If a broad area type or surface emission type semiconductor laser is employed in place of the aforementioned semiconductor laser, a high-output excitation light source can be obtained more inexpensively.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
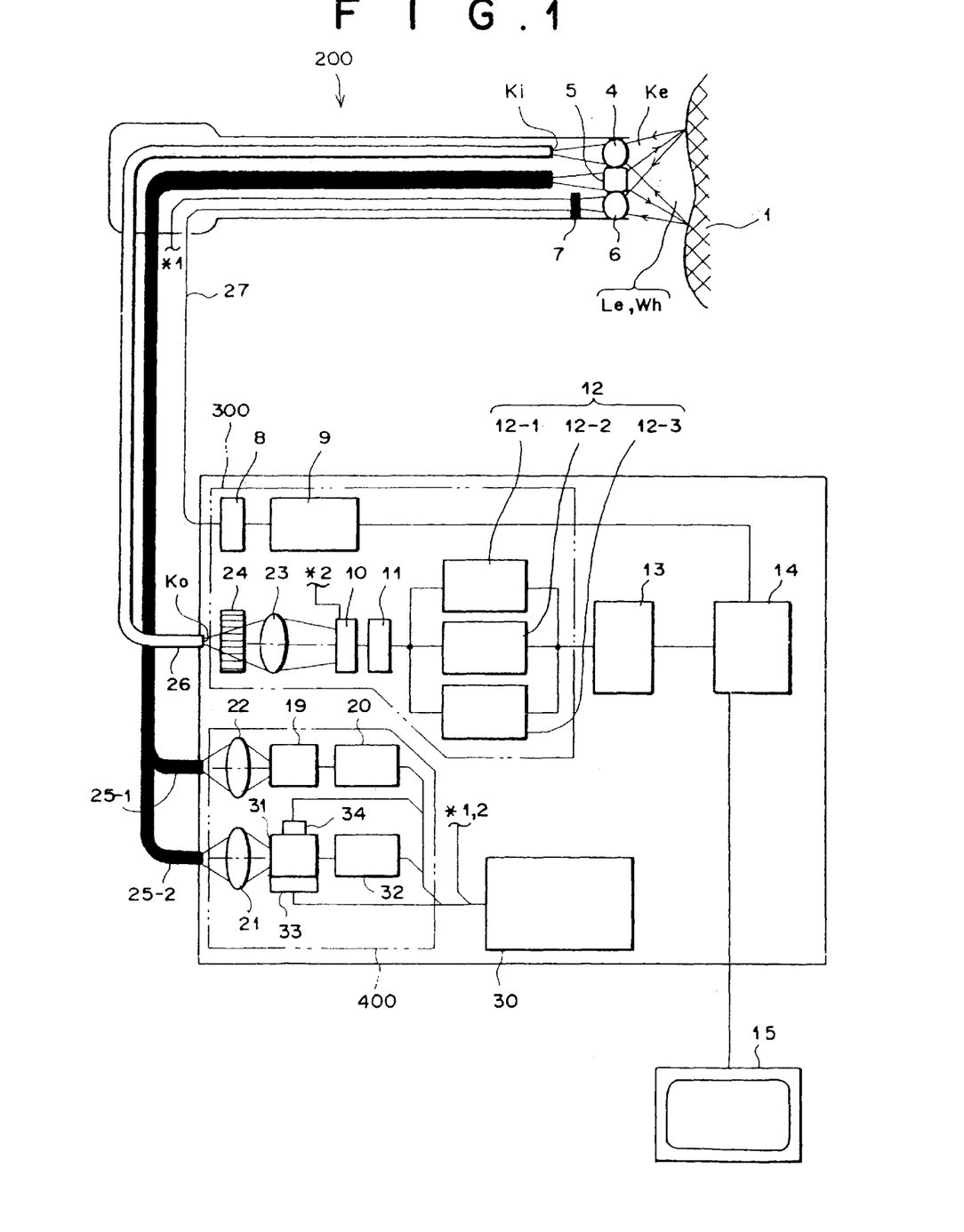
FIG. 1 is a block diagram showing a fluorescence observing apparatus constructed according to a first embodiment of the present invention.

Referring now in greater detail to the drawings and initially to FIG. 1, there is shown a fluorescence observing apparatus constructed according to a first embodiment of the present invention. The fluorescence observing apparatus comprises (1) a light source section 100 equipped with an excitation light source and a visible light (white light) source, (2) a flexible endoscope 200 for forming a normal image obtained by irradiating white light Wh guided from the light source section 100, to the tissue of an organism and also propagating the image of fluorescence (obtained by irradiating excitation light Le likewise guided from the light source section 100, to the tissue) to an optical fiber, (3) an image taking-in section 300 for taking in and storing the normal image and fluorescence image obtained by the endoscope 200, as image signals, (4) an image computing memory 13 equipped with the computation function of discriminating a cancerous tissue and a normal tissue by receiving and computing the image signals stored in the image taking-in section 300 and the storage function of storing and outputting the result of discrimination as an image signal, (5) a video signal processing circuit 14 for converting the image signal outputted from the image computation memory 13, to a video signal, (6) a display section 15 for displaying the video signal outputted by the video signal processing signal 14, as an image, and (7) a control section 16 for controlling the timings at which irradiation of the excitation light Le, irradiation of the white light Wh, reading of the normal image, reading of the fluorescence image, etc., are performed.

The white light source 19 of the light source section 100 is connected to a white-light power source 20 that is controlled by the control section 16, and the white light source 19 emits white light Wh at cycles of 1/60 sec. The white light Wh is focused by a white-light condenser lens 22 and is incident on a white-light guide 25-1. The white-light guide 25-1 is formed with a multicomponent glass fiber and connected to the light source section 100.

The excitation light source 19 of the light source section 100, on the other hand, employs an InGaN semiconductor laser of multi-quantum cell structure (active layer InGaN/InGaN). The excitation light source 19 is pulse-driven by an LD power source 20 that is controlled by the control section 16, and emits pulsed excitation light Le at cycles of 1/60 sec. The excitation light Le is focused by an excitation-light condenser lens 21 and is incident on an excitation-light guide 25-2. The excitation-light guide 25-2 is formed with a silica glass fiber and connected to the light source section 100. In addition, a Peltier element 29 and a thermistor 28 are disposed in intimate contact with the excitation light source 17 and connected to the control section 16.

Figure 2:
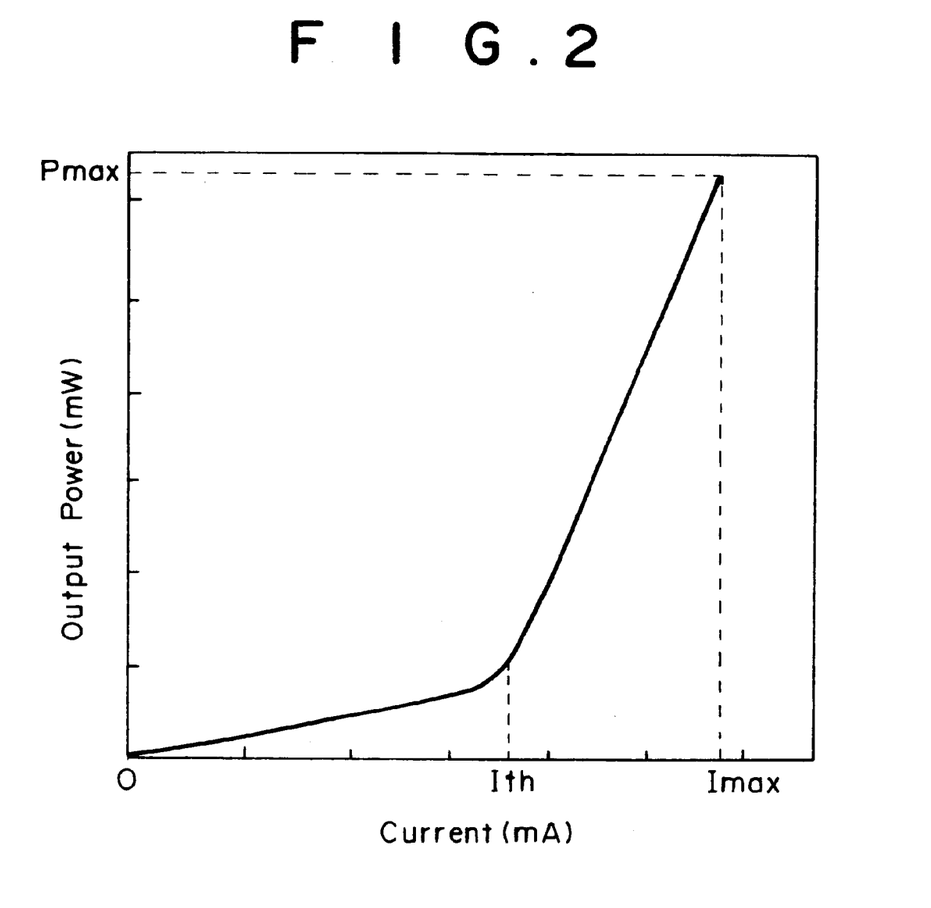
FIG. 2 is a diagram showing the power-versus-current characteristic of the semiconductor laser employed in the fluorescence observing apparatus of FIG. 1.
Figure 3:
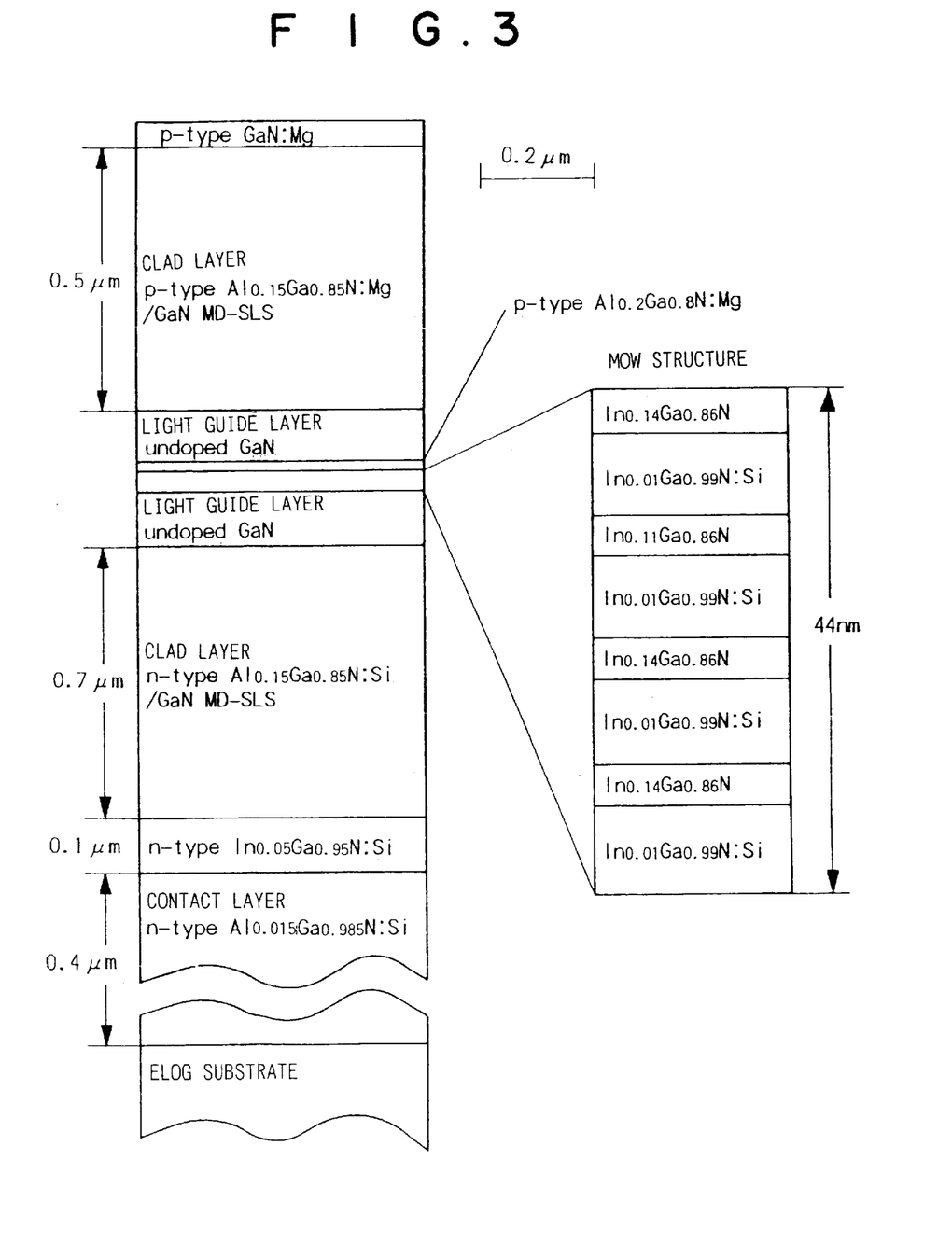
FIG. 3 is a diagram showing the internal structure of the semiconductor laser.

Note that the semiconductor laser employed in the excitation light source 17 has a continuous maximum output (continuous maximum rated output) of Pmax (mW), a continuous maximum operating current of Imax (mA), an oscillating wavelength of 410 nm (single mode), and an oscillating threshold current of Ith (mA) (Ith<Imax), as shown in FIG. 2. The structure and composition of the excitation light source 17 are shown in FIG. 3. Also, the white-light guide 25-1 and the excitation-light guide 25-2 are bundled integrally in cable form.

In the endoscope 200, the white-light guide 25-1 and the excitation-light guide 25-2 bundled integrally in cable form are inserted and disposed so that excitation light Le or white light Wh is irradiated toward a sample 1 through an illuminating lens 5. The image of the tissue 1 illuminated with white light Wh is formed on the light receiving surface of a normal-observation charge-coupled device (CCD) imager 7 through a normal-observation objective lens 6. The normal image is converted to an electrical signal by the normal-observation CCD imager 7 and transmitted to the image taking-in section 300 through a CCD cable 27. On the other hand, the image of fluorescence Ke, which occurs from the sample 1 when excitation light Le is irradiated, is formed on an end face Ki of a fluorescence image fiber 26 through a fluorescence-observation objective lens 4. The fluorescence image propagates along the fluorescence image fiber 26 and is guided to the other end face Ko of the fluorescence image fiber 26 connected to the image taking-in section 300.

For observation of a normal image, the image taking-in section 300 is provided with a normal observation A/D converter 8 for converting the electrical image signal, transmitted by the CCD cable 27, to a digital image signal and a normal image memory 9 for storing the digital image signal. For observation of a fluorescence image, the image taking-in section 300 is further provided with a fluorescence observation high-sensitivity CCD imager 10 (cooling-type back irradiation CCD imager), an optical system constructed so that the fluorescence image guided to the end face Ko of the fluorescence image fiber 26 is formed on the light receiving surface of the fluorescence observation high-sensitivity CCD imager 10 by a fluorescence condenser lens 23 through an excitation-light cut filter 24 for cutting off a wavelength less than or equal to a wavelength of near 4100 nm, a fluorescence observation A/D converter 11 for converting the electrical image signal, received and converted by the fluorescence observation high-sensitivity CCD imager 10, to a digital image signal, and a fluorescence image memory 12, which consists of a fluorescence image h1 memory 12-1, a fluorescence image h2 memory 12-2, and a fluorescence image h3 memory 12-3, for storing the digital image signal.

Figure 4:
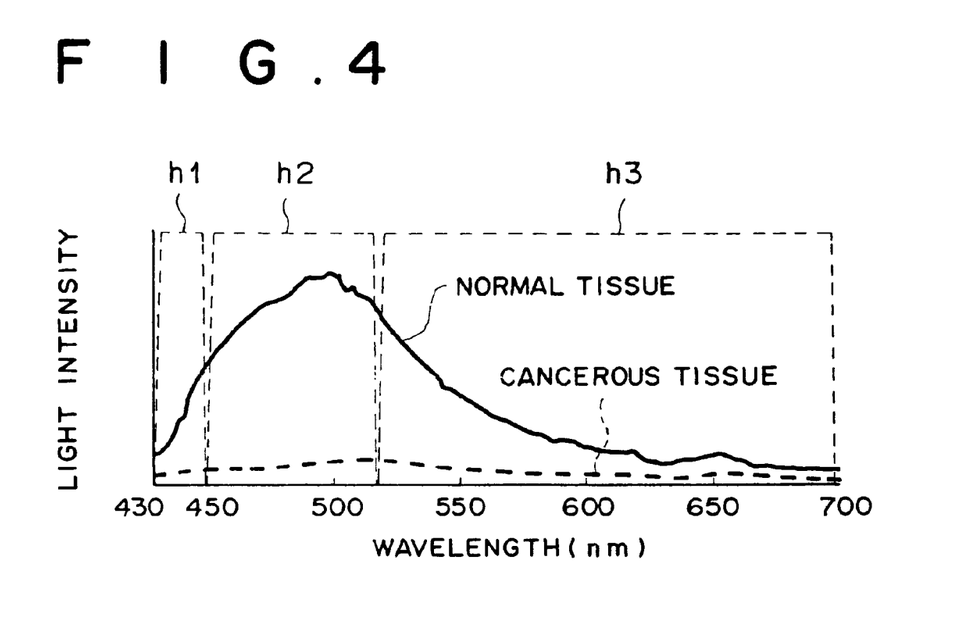
FIG. 4 is a diagram showing the wavelength regions where measurements are made and the profiles of fluorescence emitted from the tissue of an organism.
Figure 5:
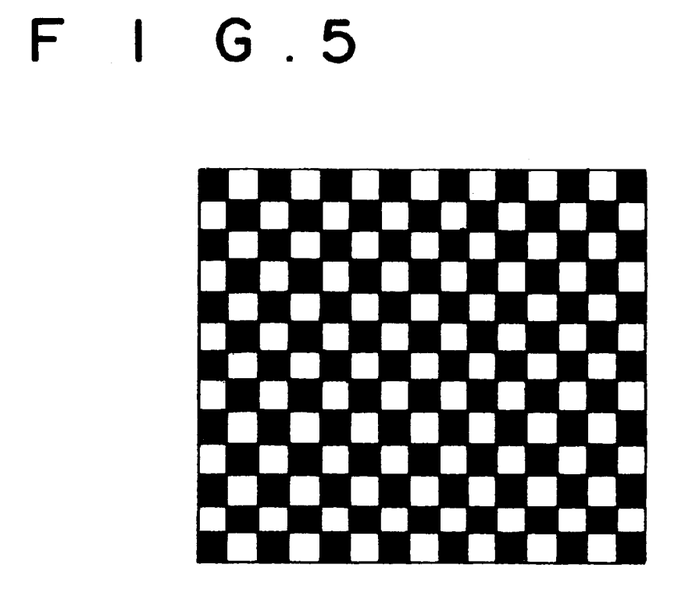
FIG. 5 is a diagram showing the structure of the mosaic filter employed in the fluorescence observing apparatus of FIG. 1.

Note that the light receiving surface of the fluorescence observation high-sensitivity CCD imager 10 has a color mosaic filter 10a such as the one shown in FIG. 5. The color mosaic filter 10a consists of sets with three kinds of filters, and the filters have a characteristic of respectively transmitting only light which has a wavelength belonging to a wavelength region h1 (near 430 nm to near 445 nm), light which has a wavelength belonging to a wavelength region h2 (near 445 nm to near 520 nm), and light which has a wavelength belonging to a wavelength region h3 (near 520 nm to near 700 nm), shown in FIG. 4. The fluorescence image is separated into the wavelength bands of the 3 regions shown in FIG. 4 and is received.

Next, a description will be given of the operation in the above-mentioned first embodiment.

Figure 6:
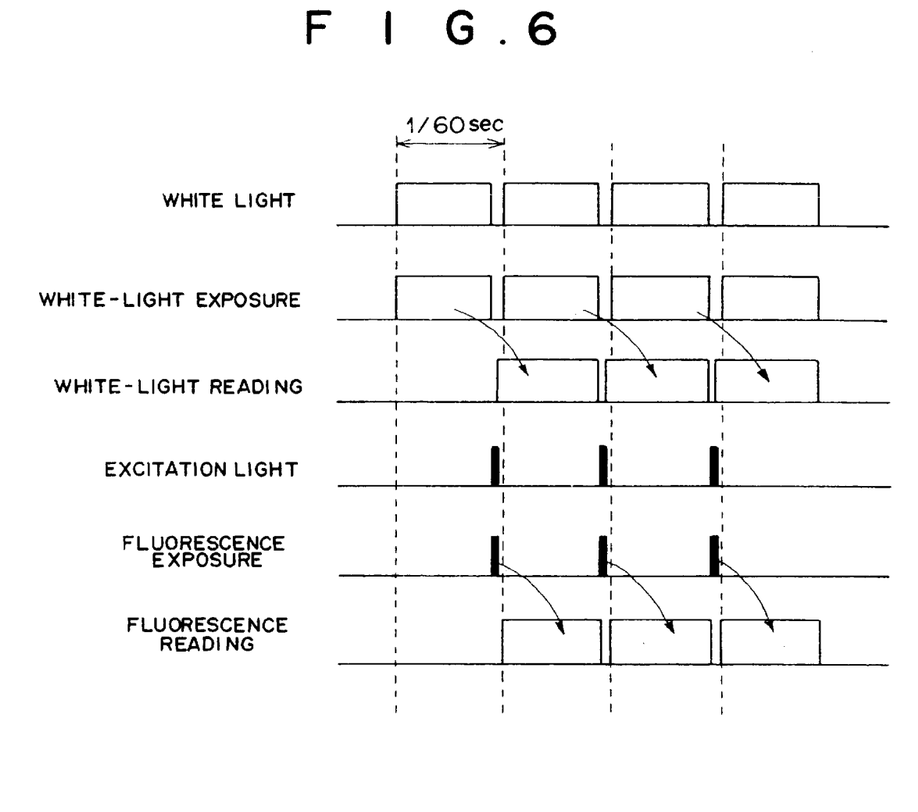
FIG. 6 is a timing chart showing the timings at which excitation light and white light are irradiated.

The fluorescence observing apparatus of the first embodiment is controlled by the controller 16 in accordance with a timing chart shown in FIG. 6. As shown in the timing chart of FIG. 6, white light Wh emitted from the white light source 19 is guided to the endoscope 200 through the white-light condenser lens 22 and the white-light guide 25-1 and illuminates the tissue 1 through the illuminating lens 5. The image of the tissue 1 illuminated with the white light Wh is formed on the light receiving surface of the normal observation CCD imager 7 by the normal-observation objective lens 6 and is exposed to the photosensitive portion of the normal-observation CCD imager 7 which consists of a plurality of photosensitive elements for converting light to electric charge. The image of the tissue 1 is converted to signal charge and accumulated. If the irradiation of the white light Wh ends, the signal charges accumulated in the photosensitive portion are converted to an electrical image signal by a circuit constituting the normal observation CCD imager 7, and the electrical image signal is read out. The electrical image signal is converted to a digital signal by the normal observation A/D converter 8 and is stored in the normal image memory 9.

If the above-mentioned irradiation of the white light Wh ends, pulsed excitation light Le emitted from the excitation light source 17 is guided to the endoscope 200 through the excitation light condenser lens 21 and the excitation light guide 25-2 and is irradiated toward the tissue 1 through the illuminating lens 5.

The fluorescence, emitted from the tissue 1 by irradiation of the excitation light Le, is formed on the end face Ki of the fluorescence image fiber 26 by the fluorescence image objective lens 4 and is propagated to the other end face Ko. With respect to the fluorescence image propagated to the end face Ko, the excitation light Le contained in the fluorescence Ke (which is a measuring object) is removed by an excitation-light cut filter 24. Then, the fluorescence image is formed on the light receiving surface of the fluorescence observation high-sensitivity CCD imager 10 having the mosaic filter 10a by the fluorescence condenser lens 23 and is exposed to the photosensitive portion of the fluorescence observation high-sensitivity CCD imager 10 and is accumulated as signal charge. If irradiation of the pulsed excitation light Le ends, the signal charges accumulated in the photosensitive portion are converted to an electrical image signal by a circuit constituting the fluorescence observation high-sensitivity CCD imager 10, and the electrical image signal is read out. The electrical image signal is converted to a digital signal by the fluorescence observation A/D converter 11 and is stored in the fluorescence image h1 memory 12-1, the fluorescence image h2 memory 12-2, and the fluorescence image h3 memory 12-3.

Note that the intensity value of the fluorescence, transmitted through the filter h1 of the mosaic filter 10*a*, and converted to a digital value by the fluorescence observation A/D converter 11, is stored in the fluorescence image h1 memory 12-1. Also, the intensity value of the fluorescence, transmitted through the filter h2 of the mosaic filter 10*a*, and converted to a digital value by the fluorescence observation A/D converter 11, is stored in the fluorescence image h2 memory 12-2. Furthermore, the intensity value of the fluorescence, transmitted through the filter h3 of the mosaic filter 10*a*, and converted to a digital value by the fluorescence observation A/D converter 11, is stored in the fluorescence image h3 memory 12-3.

Now, the operating conditions of the InGaN semiconductor laser of multi-quantum cell structure (active layer InGaN/InGaN) employed in the excitation light source 17 will be described in detail.

This semiconductor laser is driven so that the integrated value of the oscillating output values per unit time is less than or equal to the integrated value of the continuous maximum output values per unit time, and a pulse oscillation duty ratio is set so that a peak value greater than or equal to the continuous maximum output is obtained. When the above-mentioned semiconductor laser whose continuous maximum output is Pmax (mW) is pulse-operated at cycles of 1/60 sec, energy E equivalent to the integrated value of the oscillating output values of each pulse per unit time needs to be set to a value less than or equal to the integrated value J of the continuous maximum output values per unit time. Since the unit time is 1/60 sec, it becomes necessary to meet the conditions shown below.

$$\text{Energy } E \text{ of a single pulse } (mJ) \leq P\text{max}/60$$

Figure 7A:
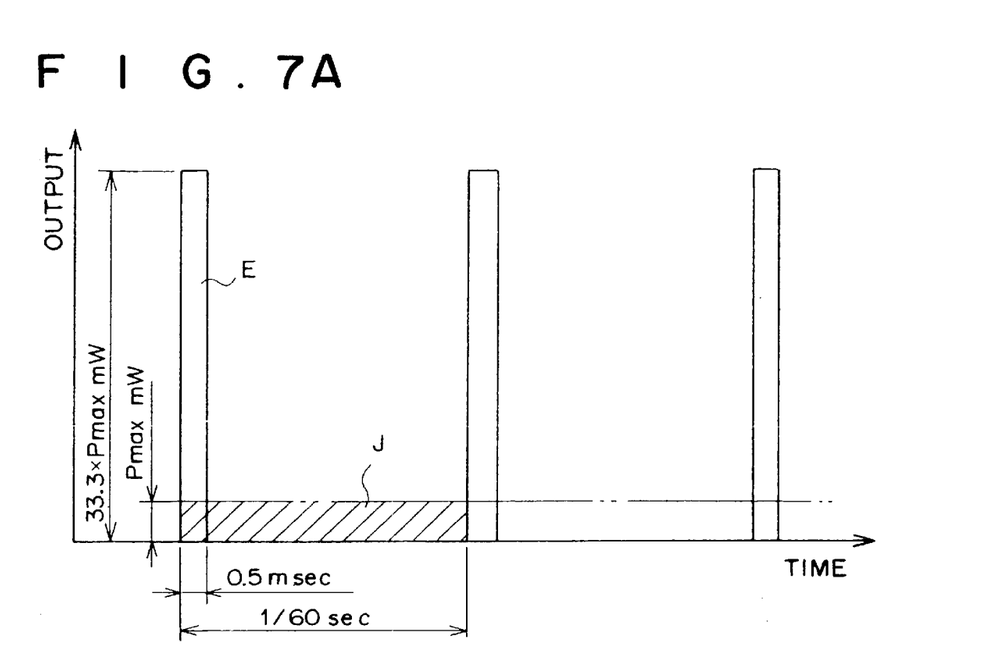
FIG. 7A is a timing diagram showing the conditions under which the semiconductor laser is driven with a pulse width of 0.5 mm.

Therefore, for example, if the pulse width of a rectangular wave generated by injection of rectangular current is made 0.5 msec, the peak value is set to the following value (see FIG. 7A).

$$\text{Peak value } P_p \ (mW) \leq (1000/0.5) \times (P\text{max}/60) \approx 33.3 \times P\text{max}$$

Figure 7B:
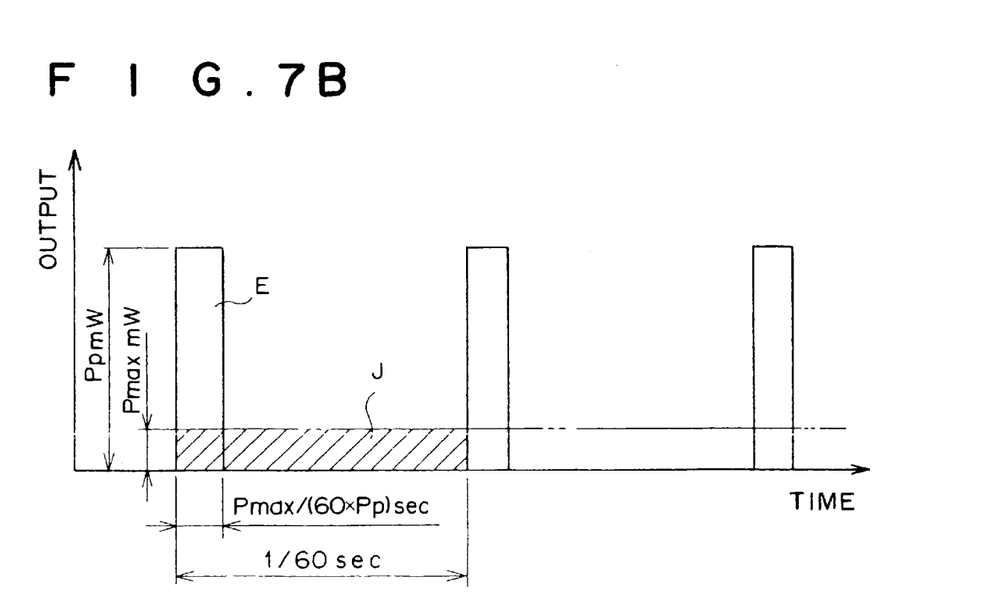
FIG. 7B is a timing diagram showing the conditions under which the semiconductor laser is driven with a peak value of 200 mm.

Also, if the peak value in the case of driving the semiconductor laser with a rectangular wave is made Pp (mW) (Pp>Pmax), the duty ratio is set so that the pulse width becomes the following value (see FIG. 7B).

$$\text{Pulse width (sec)} \leq (1/Pp) \times (P\text{max}/60) = P\text{max}/(60 \times Pp)(\text{sec})$$

Figure 8:
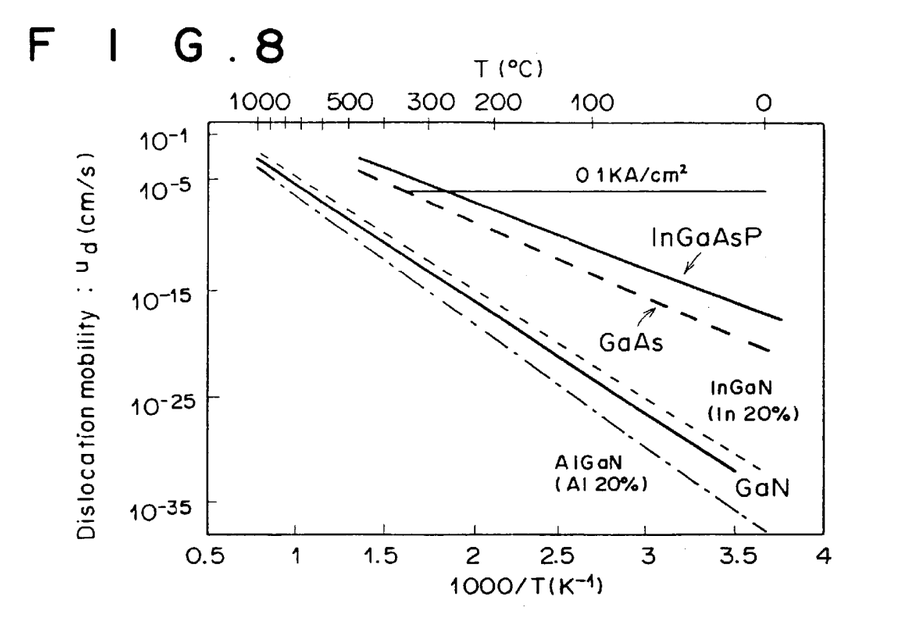
FIG. 8 is a diagram showing the temperature dependency of dislocation.

As shown in FIG. 8, InGaN is less by a factor of $10^{-10}$ in dislocation mobility at the same temperature than InGaAsP and GaAs. Also, a condition of oscillation has been alleviated because the active layer has a multi-quantum cell structure of InGaN/InGaN (i.e., luminous efficiency has been enhanced by reducing the oscillating threshold current to make temperature dependency lower). For this reason, as described above, even if the semiconductor laser is oscillated at a peak value greater than or equal to the continuous maximum output value, no catastrophic optical damage (COD) will arise and the peak value can continue high pulse oscillation with stability. In addition, the pulse drive makes the generation of heat intermittent and increases the radiating time. Therefore, because of heat generated by a crystal, doping materials, such as Mg, etc., are prevented from diffusing thermally and crossing and short-circuiting the active layer. As a result, device degradation can be prevented and device lifetime can be prolonged.

As shown in the timing chart of FIG. 6, in order to take in a normal image and a fluorescence image and obtain a dynamic image from them, it is necessary that excitation light Le and white light Wh be exposed by setting timing so that the irradiation of excitation light Le to the tissue 1 and the irradiation of white light Wh to the tissue 1 do not overlap within a period of 1/60 sec. For instance, timing needs to be set so that the irradiation of excitation light Le to the tissue 1 and the exposure of fluorescence emitted from the tissue 1 are executed during the time that the irradiation of white light Wh stops, and the time that the normal observation CCD imager 7 is in the vertical blanking period. Also, when reading out the signal charges exposed and stored in the photosensitive portion by the respective CCD imagers, the accumulated signal charges are moved and saved in a circuit other than the photosensitive portion constituting the CCD imager, and the saved signal charges are then read out. Therefore, since signal charges can be read out during a sufficient time of 1/60 sec until signal charges in the next cycle are read out, an image signal with less noise can be obtained.

The values of the image signals, stored in the fluorescence image h1 memory 12-1, the fluorescence image h2 memory 12-2, and the fluorescence image h3 memory 12-3, are output to the image computing memory 13 and subjected to the following computing process.

Figure 9:
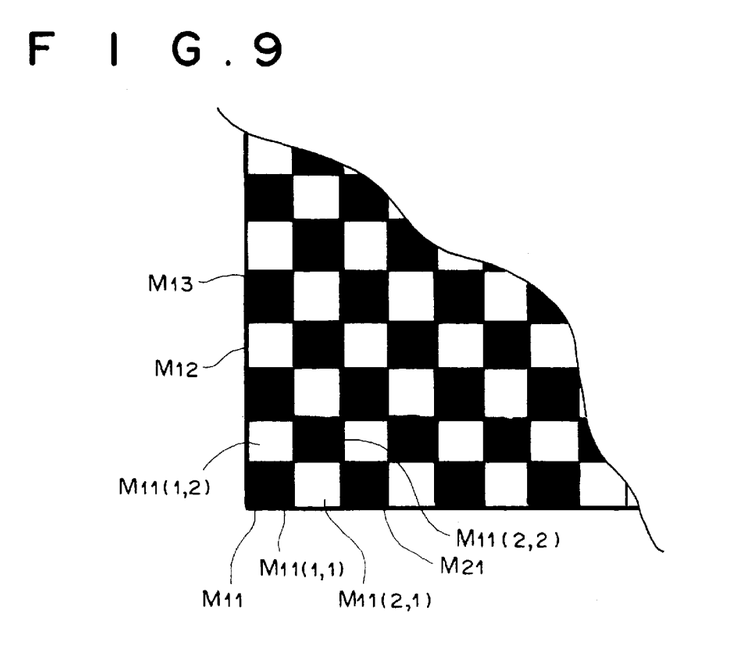
FIG. 9 is an enlarged diagram of the mosaic filter shown in FIG. 5.

As shown on an enlarged scale in FIG. 9, the mosaic filter 10*a* consists of a large number of matrix blocks having four microregions. For example, in the 4 microregions M11(1, 1), M11(1, 2), M11(2, 1), and M11(2, 2) within block M11, a filter h1, filters h2, and a filter h3 having a wavelength transmission characteristic such as that shown in FIG. 4 are disposed. More specifically, the filter hi, the filters h2, and the filter h3 transmit only light which has a wavelength belonging to a wavelength region h1, light which has a wavelength belonging to a wavelength region h2, and light which has a wavelength belonging to a wavelength region h3, respectively. The filer h1 corresponds to the microregion M11(1, 1), the filters h2 to the microregions M11(1, 2) and M11(2, 1), and the filter h3 to the microregion M11(2, 2). Since it is generally known that, as shown in FIG. 4, at the wavelength region h2 a normal tissue is different in profile from a cancerous tissue, discrimination between a normal tissue and a cancerous tissue becomes possible by dividing the fluorescence intensity at the wavelength h2 by the fluorescence intensity at the overall wavelength region. That is, if the intensity values of fluorescence, obtained from the individual photosensitive elements corresponding to the 4 microregions M11(1, 1), M11(1, 2), M11(2, 1),and M11(2, 2) within the block M11 of the mosaic filter 10*a*, are taken to be D11(1, 1), D11(1, 2), D11(2, 1), and D11(2, 2), a discrimination value DD11 for the block M11 is represented as follows:

$D11$=fluorescence intensity transmitted through filter $h2$/fluorescence intensity at the overall wavelength region =fluorescence intensity transmitted through filter $h2$/(fluorescence intensity transmitted through filter $h1$+fluorescence intensity transmitted through filter $h2$+fluorescence intensity transmitted through filter $h3$)

=[{$D11(1, 2)$+$D11(2, 1)$}/2]/[$D11(1, 1)$+{$D11(1, 2)$+$D11(2, 1)$}/2+ $D11(2, 2)$]

The discrimination value calculated in the above-mentioned manner is obtained for all the blocks of the mosaic filter 10*a*, that is, M11, M12, M13, M14, . . . The discrimination value is compared with a reference discrimination value ST calculated in the same manner as the aforementioned method from a tissue judged to be a cancerous tissue or normal tissue, whereby a degree of difference can be obtained as a value. The result is stored in the image computing memory 13 as a differential discrimination value SS. That is, a differential discrimination value SS for block Mxy is calculated by the following equation:

$$SS(x, y)=DDxy-ST$$

The differential discrimination value SS calculated as described above is output from the image computing memory 13 and is input to the video signal processing circuit 14 along with the value of the image signal of the normal image outputted from the normal image memory 9. These signal values are processed so that the normal image and the fluorescence image are simultaneously displayed on a single screen, and are output and displayed on the display section 15 as information that is used for diagnosing a morbid part.

A thermistor 28 senses the temperature of the excitation light source 17 at all times and outputs the sensed temperature to the control section 16. The control section 16 drives a Peltier element 29 to cool the excitation light source 17, if the temperature of the excitation light source 17 approaches 20° C. Because of this, the temperature of the excitation light source 17 never exceeds 20° C. at any time, during the time that the fluorescence observing apparatus is operating.

Because of the above-mentioned operation, the temperature of the InGaN semiconductor laser (active layer InGaN/InGaN) is always maintained at 20° C. or less. The oscillating threshold current in the InGaN semiconductor laser decreases in dependence on temperature and the maximum output is not limited at thermal saturation. Therefore, the InGaN semiconductor laser oscillates at a higher peak value. In addition, because the degradation rate of InGaN semiconductor laser becomes lower in accordance with temperature, oscillation over a long time becomes possible. As a result, the lifetime of the excitation light source 17 employing the InGaN semiconductor laser can be appreciably prolonged.

Note that by cooling the InGaN semiconductor laser to 10° C. or less, oscillation over a long time becomes possible with higher output. Also, if a multi-stage Peltier element is employed to cool the InGaN semiconductor laser down to −20° C., the above-mentioned effect can be further enhanced.

While, in the above-mentioned first embodiment, the InGaN semiconductor laser of multi-quantum cell structure (active layer InGaN/InGaN) is employed, the above-mentioned same effect which is superior to the conventional case can be obtained even in other InGaN-based semiconductor lasers and GnN-system semiconductor lasers.

In addition, in the case where a single semiconductor laser gives rise to underoutput, the desired output can be obtained by driving a plurality of semiconductor lasers in parallel.

Figure 10:
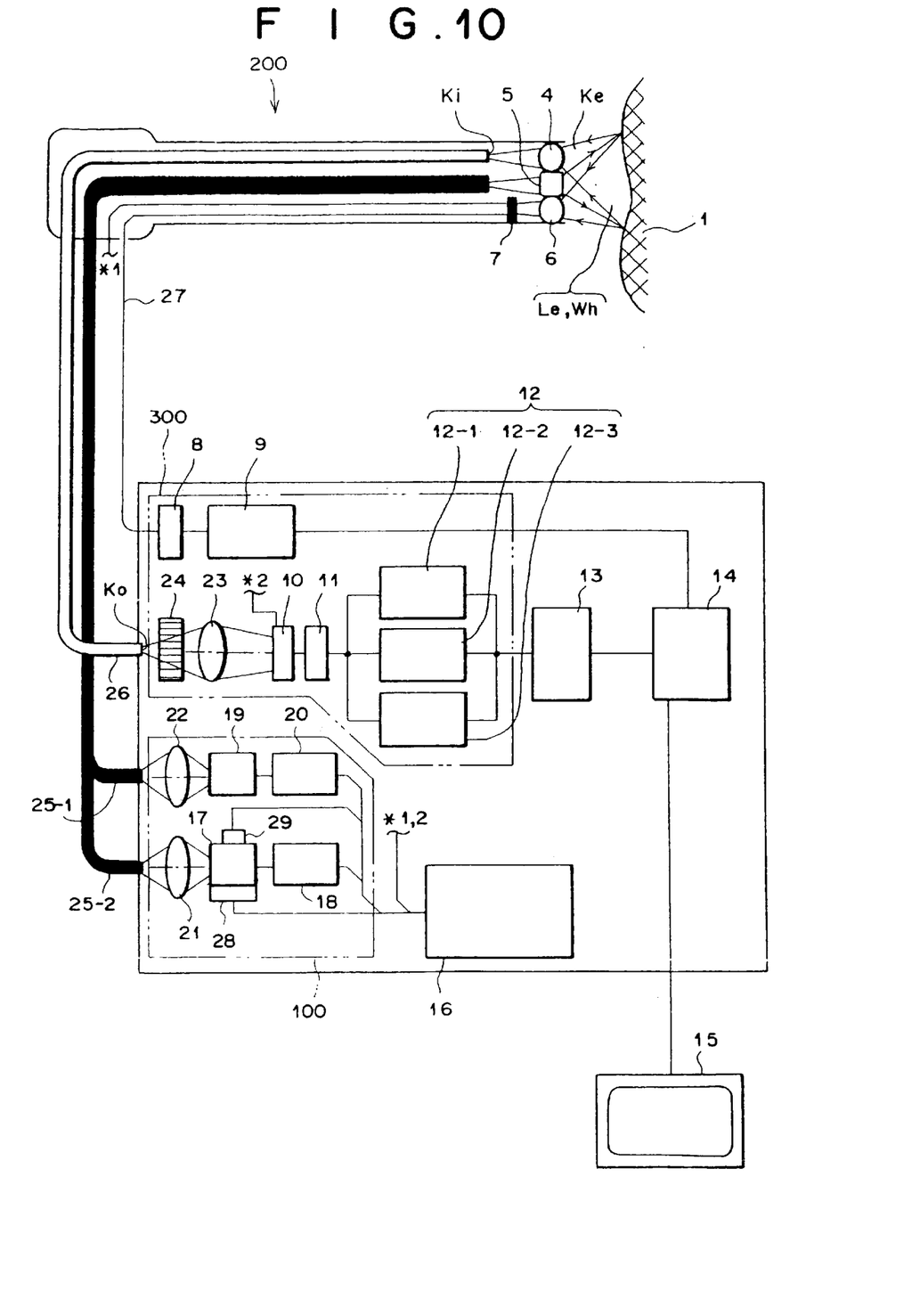
FIG. 10 is a block diagram showing a fluorescence observing apparatus constructed according to a second embodiment of the present invention.

FIG. 10 illustrates a fluorescence observing apparatus constructed according to a second embodiment of the present invention. This fluorescence observing apparatus includes an excitation light source, which consists of 5 (five) InGaN semiconductor lasers of multi-quantum cell structure, and temperature controlling means for controlling the temperature of the excitation light source. The excitation light source is capable of emitting high-output excitation light intermittently.

The fluorescence observing apparatus of the second embodiment comprises a light source section 100 equipped with an excitation light source and a white light source, an endoscope 200, an image picking-up section 300, an image computing memory 13, a video signal processing circuit 14, a display section 15, and a control section 30 for controlling the timings at which irradiation of excitation light Le, irradiation of white light Wh, reading of a normal image, reading of a fluorescence image, etc., are performed.

Note that the same reference numerals and characters will be applied to the same components as the first embodiment shown in FIG. 1 and therefore a detailed description thereof will be omitted unless particularly necessary.

The white light source 19 of the light source section 400 is connected to a white-light power source 20 that is controlled by the control section 30. The white light Wh emitted from the white light source 19 is focused by a white-light condenser lens 22 and is incident on a white-light guide 25-1.

On the other hand, an excitation light source 31 is constituted of five InGaN semiconductor lasers of multi-quantum cell structure (active layer InGaN/InGaN) and is pulse-driven by an LD power source 20 that is controlled by the control section 30. The excitation light Le emitted from the excitation light source 31 is focused by an excitation-light condenser lens 21 and is incident on an excitation-light guide 25-2. In addition, a Peltier element 34 and a thermistor 33 are disposed in intimate contact with the excitation light source 31 and are both connected to the control section 30.

Note that each of the InGaN semiconductor lasers of multi-quantum cell structure constituting the excitation light source 31 has a continuous rated output of 5 mW at room temperature, an oscillating wavelength of 410 nm (single mode), and an oscillating threshold current of 50 mA. The structure of the semiconductor laser is the same as the excitation light source shown in FIG. 1 and operated with a dc bias current greater than or equal to the oscillating threshold current 50 mA.

Next, a description will be given of the operation of the endoscope in the second embodiment. The operation of the second embodiment is almost the same as that of the first embodiment shown in FIG. 1, except for the operation other than the operation associated with the light source section 400. Therefore, the operation associated with the light source section 400 will be primarily described.

Figure 11:
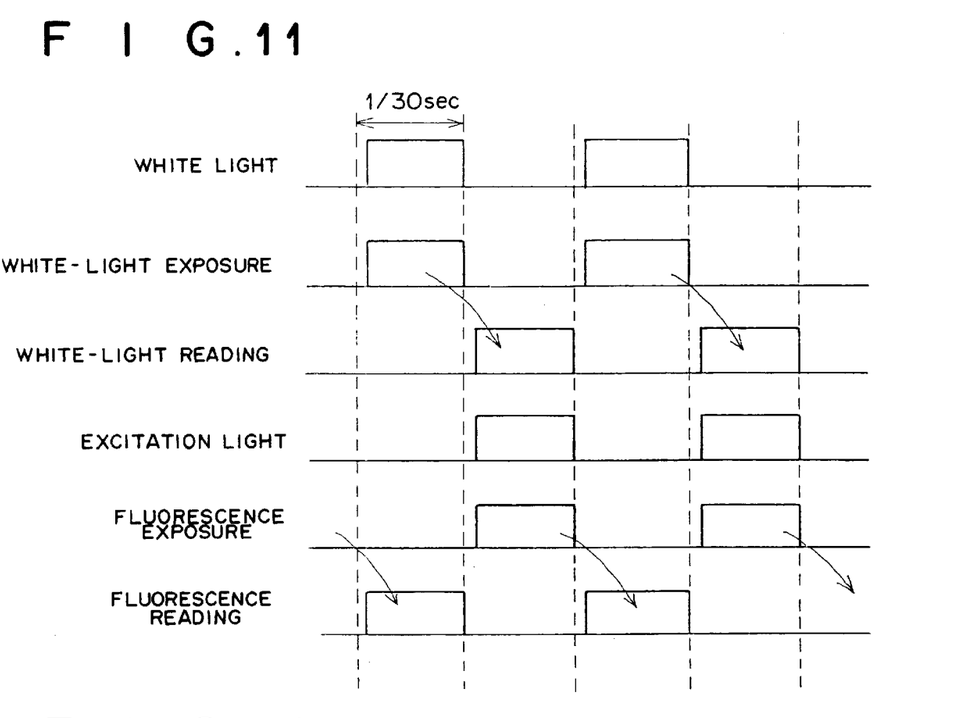
FIG. 11 is a timing chart showing the timings at which excitation light and white light are irradiated.

The fluorescence observing apparatus of the second embodiment is controlled by the control section 30 in accordance with a timing chart shown in FIG. 11. (1) The irradiation of white light Wh and the exposure of a normal image by the normal observation CCD imager 7 and (2) the irradiation of excitation light Le and the exposure of a fluorescence image by the fluorescence observation CCD imager 10 are alternately performed at cycles of 1/30 sec. According to the control performed by the control section 30, a signal at the time of the formation of a normal image is input to a normal observation A/D converter 8, and a signal at the time of the formation of a fluorescence image is input to a fluorescence observation A/D converter 11.

Therefore, a normal image and a fluorescence image are obtained at cycles of 1/15 sec, and the normal image and fluorescence image displayed on the display section 15 are displayed as a dynamic image in which updating is performed at cycles of 1/15 sec.

The thermistor 33 senses the temperature of the excitation light source 31 at all times and outputs the sensed temperature to the control section 30. The control section 30 drives the Peltier element 34 to cool the excitation light source 31, if the temperature of the excitation light source 31 approaches 20° C. Because of this, the temperature of the excitation light source 31 never exceeds 20° C. at any time, during the time that the fluorescence observing apparatus is operating. The remaining operation of the second embodiment is the same as the first embodiment shown in FIG. 1.

Figure 12:
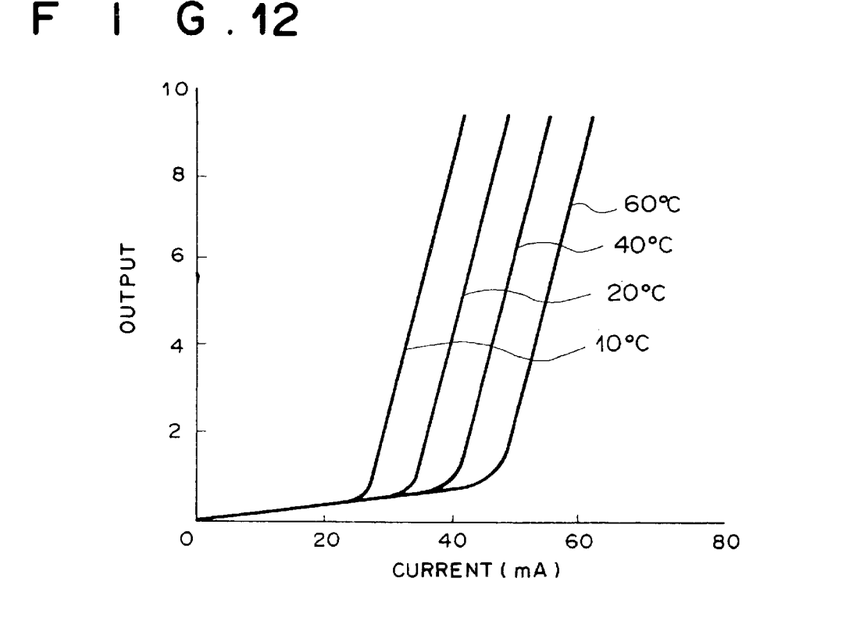
FIG. 12 is a diagram showing the relationship between the operating temperature, the drive current, and the output.

FIG. 12 shows the relationship between the operating temperature and the continuous oscillating output in the InGaN semiconductor laser of multi-quantum cell structure constituting the excitation light source 31. The oscillating threshold current decreases in accordance with temperature, and if temperature gets lower and lower, then the maximum output is not limited at thermal saturation. Therefore, it is found that higher output is obtained.

That is, if the operating temperature is cooled to 20° C. or less, an output of approximately 15 mW is obtained with a drive current of 50 mA, even if the rated output of the semiconductor laser is 5 mW at room temperature. In addition, since the fluorescence observing apparatus in the second embodiment intermittently emits excitation light, the influence of thermal saturation is alleviated and therefore higher-output excitation light is obtained.

That is, excitation light with a high output of near 100 mW is obtained from the excitation light source 31, and sufficient output is obtained in actually observing fluorescence.

Figure 13:
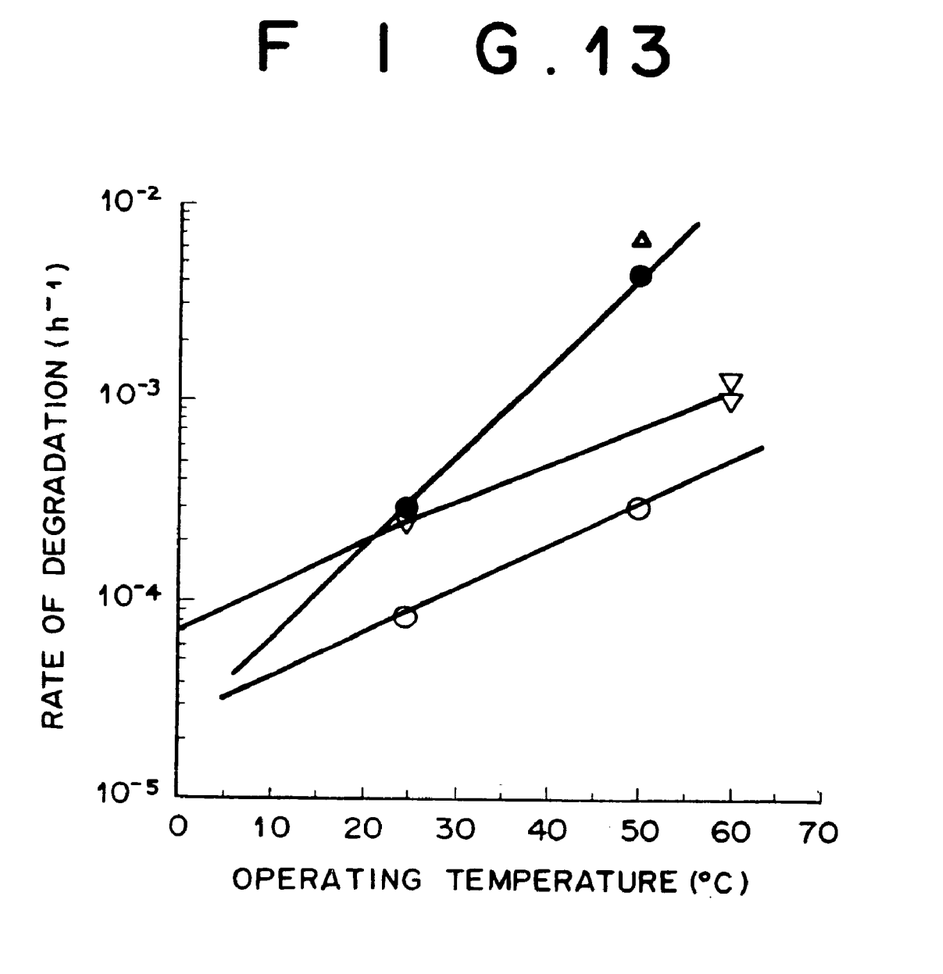
FIG. 13 is a diagram showing the relationship between the operating temperature and the rate of degradation.

FIG. 13 shows the relationship between the operating temperature and the rate of degradation in the InGaN semiconductor laser of multi-quantum cell structure constituting the excitation light source 31, and shows the rate of degradation when the above-mentioned InGaN semiconductor laser is oscillated with an output of 30 mW.

That is, it is found that even when the semiconductor laser is oscillated with a high output of 30 mW, a sufficiently long lifetime is obtained if the operating temperature is maintained at 20° C. or less.

As described above, if an InGaN-based semiconductor laser is employed in place of the aforementioned GaN-based semiconductor laser, carriers are inevitably captured at a local level formed due to the composition unevenness of indium (In), etc., before they are captured at a lattice defect from which non-radiative recombination occurs. At the local level, radiative recombination is efficiently performed. Therefore, even if a defect such as dislocation is present, non-radiative recombination will not occur from the defect and the injected current can be prevented from giving rise to generation of heat without being converted to light. As a result, even if a defect such as dislocation is present within the active layer, the occurrence of catastrophic optical damage (COD) can be prevented. Thus, an excitation light source for intermittently emitting high-output excitation light in the desired wavelength band can be obtained.

If the active layer of the aforementioned semiconductor laser has an InGaN/InGaN quantum cell structure, a quantum level is formed in the quantum cell and carriers become concentrated in the mini-band. As a result, because the efficiency of radiative recombination becomes better and the oscillating threshold current is reduced, higher light output can be obtained with less drive current and an excitation light source with even higher output can be obtained.

While the control section 30 in the second embodiment controls the excitation light source 31 so that it is maintained at 20° C. or less, as a variation the excitation light source 31 can be maintained at 10° C. or less. In this case, as shown in FIG. 12, if the InGaN semiconductor laser of multi-quantum cell structure constituting the excitation light source 31 is driven with a drive current of 50 mA, the semiconductor laser is oscillated with a high output of 30 mW or greater and therefore a high output of 150 mW or greater in total is obtained. As shown in FIG. 13, even in the case where the semiconductor laser is oscillated with an output of 30 mW, the rate of degradation is about $10^{-4}$ $(h^{-1})$ if the operating temperature is 10° C. or less. Thus, the semiconductor laser has a lifetime of 1000 hrs and is therefore able to ensure a necessary lifetime in actual operating circumstances. Since the above-mentioned description for the operation has been performed with a continuous rated output of 5 mw as reference, the output has been represented in units of mW. However, because the actual irradiation time of excitation light is 0.5 sec or less for 1 sec, the output per unit time is one-half or less of the output described above.

While it has been described in the second embodiment that the single-mode GaN semiconductor laser is employed as an excitation light source, a GaN broad area type semiconductor laser, GaN surface emission type semiconductor laser, or array type semiconductor laser may be employed in place of the single-mode GaN semiconductor laser. By employing these semiconductor lasers, an inexpensive and high-output excitation light source can be obtained. While it has also been described that a combination of 5 semiconductor lasers is employed as an excitation light source, a single semiconductor laser may be used if a single output is sufficient for the excitation light source.

While, in each of the above-mentioned embodiment, the fluorescence observing apparatus has been applied to the aforementioned fluorescence endoscope for observing self-fluorescence emitted from the tissue of an organism not absorbing a drug such as a fluorescent dye, the present invention is not limited to the fluorescence endoscope. For example, the present invention is also applicable to a fluorescence endoscope, etc., for diagnosing the localization of a morbid part from a difference in the emitted state of the fluorescence emitted from a tissue absorbing photofurin II (which is a fluorescent dye) by irradiating excitation light to the tissue. Furthermore, the present invention is applicable to an operation microscope, a colposcope, etc.

While, in each of the above-mentioned embodiments, the GaN semiconductor laser that oscillates at a wavelength of 410 nm is employed as the aforementioned excitation light source, the present invention is not limited to the GaN semiconductor laser. For instance, a GaN semiconductor laser which oscillates at a wavelength of 380 to 440 nm can be employed where appropriate.

Although the present invention has been described with reference to the preferred embodiments thereof, the invention is not to be limited to the details given herein, but may be modified within the scope of the appended claims.

In addition, all of the contents of the Japanese Patent Application Nos. 11(1999)-192487 and 2000-143700 are incorporated into this specification by reference.

What is claimed is:

1. A fluorescence observing apparatus comprising:
   a light source for emitting excitation light;
   excitation light irradiation means for irradiating said excitation light to a sample; and
   fluorescence measurement means for measuring fluorescence emitted from said sample by the irradiation of said excitation light,
   wherein a GaN-based semiconductor laser is employed as said light source and said apparatus further includes temperature-controlling means for controlling temperature of said semiconductor laser to 20° C. or less.

2. The fluorescence observing apparatus as set fourth in claim 1, wherein said semiconductor laser emits output light greater than or equal to rated output at room temperature.

3. The fluorescence observing apparatus as set forth in claim 1, wherein said GaN-based semiconductor laser is an InGaN-based semiconductor laser.

4. The fluorescence observing apparatus as set forth in claim 2, wherein said GaN-based semiconductor laser is an InGaN-based semiconductor laser.

5. The fluorescence observing apparatus as set forth in claim 3, wherein an active layer of said semiconductor laser has an InGaN/InGaN quantum cell structure.

6. The fluorescence observing apparatus as set forth in claim 1, wherein said semiconductor laser is a broad area type semiconductor laser.

7. The fluorescence observing apparatus as set forth in claim 2, wherein said semiconductor laser is a broad area type semiconductor laser.

8. The fluorescence observing apparatus as set forth in claim 3, wherein said semiconductor laser is a broad area type semiconductor laser.

9. The fluorescence observing apparatus as set forth in claim 5, wherein said semiconductor laser is a broad area type semiconductor laser.

10. The fluorescence observing apparatus as set forth in claim 1, wherein said semiconductor laser is a surface emission type semiconductor laser.

11. The fluorescence observing apparatus as set forth in claim 2, wherein said semiconductor laser is a surface emission type semiconductor laser.

12. The fluorescence observing apparatus as set forth in claim 3, wherein said semiconductor laser is a surface emission type semiconductor laser.

13. The fluorescence observing apparatus as set forth in claim 5, wherein said semiconductor laser is a surface emission type semiconductor laser.

14. The fluorescence observing apparatus as set forth in claim 1, wherein said semiconductor laser is an array type semiconductor laser.

15. The fluorescence observing apparatus as set forth in claim 2, wherein said semiconductor laser is an array type semiconductor laser.

16. The fluorescenc[0085] observin apparatus as set forth in claim 3, wherein said semiconductor laser is an array type semiconductor laser.

17. The fluorescenc[0085] observin apparatus asset forth in claim 5, wherein said semiconductor laser is an array type semiconductor laser.

18. A fluorescence observing apparatus comprising:

a GaN-based semiconductor laser for emitting excitation light;

excitation light irradiation device for irradiating said excitation light to a sample;

temperature sensor disposed adjacent to the semiconductor laser; and cooling device responsive to an output of the temperature sensor to control the temperature of the semiconductor laser to 20 degrees C. or less.

19. The fluorescence observing apparatus of claim 18, wherein the semiconductor laser emits output light greater than or equal to rated output at room temperature.

20. The fluorescence observing apparatus of claim 18, wherein an active layer of said semiconductor laser has an InGaN/InGaN quantum cell structure.

21. The fluorescence observing apparatus of claim 20, wherein the semiconductor laser is a surface emission type laser.

22. The fluorescence observing apparatus of claim 18, wherein the cooling device is responsive to an output of the temperature sensor to control the temperature of the semiconductor laser to 10 degrees C. or less.

* * * * *